United States Patent [19]

Hardies et al.

[11] 4,113,878

[45] Sep. 12, 1978

[54] CONTROL OF PATHOGENIC FUNGI WITH FLUORINATED CARBONATES

[75] Inventors: Donald E. Hardies, Wadsworth; Jay K. Rinehart, Akron, both of Ohio

[73] Assignee: PPG Industries, Inc., Pittsburgh, Pa.

[21] Appl. No.: 784,874

[22] Filed: Apr. 5, 1977

Related U.S. Application Data

[60] Continuation-in-part of Ser. No. 505,419, Sep. 12, 1974, Pat. No. 4,022,609, which is a division of Ser. No. 299,968, Oct. 24, 1972, Pat. No. 3,852,464, which is a division of Ser. No. 76,275, Sep. 28, 1970, Pat. No. 3,742,010.

[51] Int. Cl.$^2$ .................. A01N 9/20

[52] U.S. Cl. .................. 424/301

[58] Field of Search .................. 424/301

[56] References Cited

U.S. PATENT DOCUMENTS

| | | | |
|---|---|---|---|
| 3,234,260 | 2/1966 | Pianka et al. | 260/463 |
| 3,359,296 | 12/1967 | Newallis et al. | 260/445 |
| 3,742,010 | 6/1973 | Hardies et al. | 260/463 |
| 3,852,464 | 12/1974 | Hardies et al. | 424/301 |
| 4,022,609 | 5/1977 | Hardies et al. | 71/106 |

*Primary Examiner*—Leonard Schenkman
*Attorney, Agent, or Firm*—Robert J. Grassi; George D. Morris; Irwin M. Stein

[57] ABSTRACT

Fluorinated carbonates are described which are useful to control fungus. Examples of the fluorinated carbonates are 2',4'-dinitro-6'-sec-butylphenyl 2,2,2-trifluoroethyl carbonate, 2',4'-dinitro-6'-sec-butylphenyl 2,2,3,3-tetrafluoropropyl carbonate, and 2',4'-dinitro-6'-cyclohexylphenyl 2,2,3,3-tetrafluoropropyl carbonate.

38 Claims, No Drawings

CONTROL OF PATHOGENIC FUNGI WITH FLUORINATED CARBONATES

CROSS REFERENCE TO RELATED APPLICATIONS

This application is a continuation-in-part of application Ser. No. 505,419, filed Sept. 12, 1974 and now U.S. Pat. No. 4,022,609 issued May 10, 1977, which is a divisional application of application Ser. No. 299,968, filed Oct. 24, 1972, now U.S. Pat. No. 3,852,464, issued Dec. 3, 1974, which is a division of application Ser. No. 76,275, filed Sept. 28, 1970, now U.S. Pat. No. 3,742,010, issued June 26, 1973.

BACKGROUND OF THE INVENTION

1. Field of the Invention

The invention concerns control of fungi with fluorinated carbonates, particularly substituted phenyl fluorinated carbonates.

2. Description of the Prior Art

Fungi require control because they devastate crops. One method of control is to apply a fungicide to the plants either before the occurrence of a fungicidal disease or at the time the fungicidal disease occurs. However, there are millions of pathogenic fungi which require control and which interact differently with chemicals, so that it is difficult to predict which of the many thousands of chemical compounds would result in controlling a particular fungus. Consequently it requires the continual discovery and development of new chemical compositions which are useful in the control of fungi as well as the continual study and evaluation of chemicals to determine which fungus is controlled by a compound. There is nothing in the following prior art which teaches those skilled in the art whether or not the compounds of this invention will control pathogenic fungus or/and their effects upon plants particularly the fungus disclosed herein. For example, Sherer et al, U.S. Pat. No. 3,130,037, discloses alkyl substituted dinitro phenyl fatty acid esters for controlling plant growth. Pianka et al, U.S. Pat. No. 3,234,260, discloses that isopropyl 2,4,6-sec-butylphenyl carbonate has pesticidal activities in one or more capacities, such as acaricidal, ovicidal, fungicidal, and insecticidal, but is silent on the use of fluorinated compounds to control the fungus causing Bean Rust, Safflower Rust, and Rice Blast Diseases. Pianka et al, U.S. Pat. No. 3,453,318, discloses 2-tert-butyl-5-methyl-4,6-dinitrophenylcarboxylates as being useful as selective preemergence herbicides. Donnager et al, U.S. Pat. No. 3,636,037, discloses that 4-nitrophenyl derivatives of fatty acids or of cycloalkyls and alkyls are useful for herbicidal activity. Newallis et al, U.S. Pat. No. 3,359,296, discloses insecticides which are fluoroalkyl carbonates. Abbott Laboratories' French Pat. No. 1,292,937, discloses a new process for preparing fluorinated carbonates, which carbonates are effective for reducing muscular tension and are useful as tranquilizing agents. None of the above prior art teaches one skilled in the art that the fluorinated carbonates disclosed herein may be used in a method for controlling fungus, or their affects upon plants, particularly fungus which cause diseases such as Bean Rust, Safflower Rust, Rice Blast Disease, Fusarium Wilt of Tomatoes, or Late Blight of Tomatoes.

DISCLOSURE

In accordance with this invention, there are provided carbonates which are effective to control fungi.

Carbonates here contemplated may be represented by the formula:

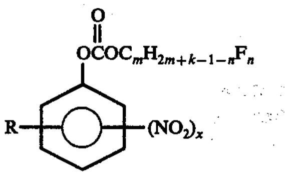

(I)

wheein:

$x$ is 1, 2, or 3;

$k$ is $-2$, 0, or 2;

$m$ is an integer ranging from 1 to 15 when $k$ is 2;

$m$ is an integer ranging from 2 to 15 when $k$ is 0 or $-2$;

$n$ is an integer ranging from 1 to $(2m+k-1)$; and

R is hydrogen, lower alkyl, halo lower alkyl, lower alkenyl, halo lower alkenyl, lower alkylthio, halo lower alkylthio, lower alkenylthio, halo lower alkenylthio, lower cycloalkyl, or halo lower cycloalkyl.

The value for $k$ depends upon the type of bonding in the $-C_mH_{2m+k-1-n}F_n$ radical, as used herein and in the claims. In general, for aliphatic straight or branched chain radicals $$k = 2-2d-4t$$

where $d$ is the number of double bonds in the radical, and $t$ is the number of triple bonds in the radical.

Thus, for aliphatic, straight, or branched chain radicals when $k = 2$ the radical is a fluoroalkyl, when $k = 0$ the radical is a fluoroalkenyl, and when $k = -2$ the radical is a fluoroalkynyl. Most often, $k = 2$.

Thus when the value of $k = 2$, and $m$ is an integer ranging from 1 to 15 and $n$ is an integer ranging from 1 to 31, the radical $-C_mH_{2m+k-1-n}F_n$, as used herein and in the claims is $-CH_2F$, when $m$ is 1, $n$ is 1, and $k$ is 2, and the radical is $-C_{15}F_{31}$ when $m$ is 15, $n$ is 31, and $k$ is 2.

For the control of pathogenic fungi, and/or for the prevention of the establishment of a pathogenic fungi population in a region, as described herein it is preferred that the radical $-C_mH_{2m+k-1-n}F_n$ be selected from the group of fluorinated radicals consisting of $-CH_2CF_2CF_2H$, $-CH_2CH_2F$, $-CH_2CF_3$, and $-CH(CF_3)_2$.

R typically contains up to 8 carbon atoms. It ordinarily is a straight or branched lower alkyl group or halo lower alkyl group having 1 to 8 carbon atoms. Often such groups having from 1 to 4 carbon atoms are used and preferably tert-butyl and sec-butyl are used. The secondary-butyl group is the most preferred group. When R is lower cycloalkyl or halo lower cycloalkyl, it ordinarily contains from 3 to 8 carbon atoms, and from 3 to 6 is preferred. Of these cyclic groups, cyclohexyl and cyclopropyl are most preferred.

When R is halo substituted, the halo substituents are usually fluoro, chloro, bromo, and/or iodo. Chloro and/or fluoro are preferred.

The value of $m$ may range from 1 to 15 or more; however, ranges from 2 to 11 or from 3 to 11 are more common and ranges from 1 to 5 are preferred. When the value of $k$ is other than 2, $m$ cannot be 1.

While the value of $n$ may range from 1 to $(2m+k-1)$, $n$ usually ranges from 3 to $(2m+k-1)$. Often $n$ is 3 or 4 and from 3 to 8 is preferred. The value of $n$ is also frequently an even integer ranging from 4 to 20.

The nitro groups and R may be located in any position on the ring. Often the phenyl ring is substituted by two nitro groups. While these groups may be located in any position, it is preferred that they be located in the 2',4'-positions. Although R may be located in any of the 3',5' or 6'-positions when nitro groups are in the 2',4'-postions, the preferred location for R is the 6'-position under such circumstances. When the criteria are met, a class results which may be represented by the following formula:

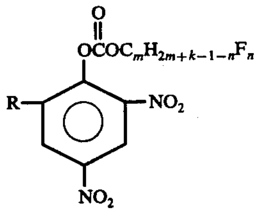
(II)

wherein:

- $m$ is an integer ranging from 1 to 15, more usually ranging from 2 to 11 or 3 to 11 and preferably from 1 to 5;
- $n$ is an integer ranging from 1 to $(2m+k-1)$; and
- R is hydrogen, lower alkyl, or halo lower alkyl ordinarily containing from 1 to 8 carbon atoms or cycloalkyl or halo cycloalkyl ordinarily containing from 3 to 8 carbon atoms. When R is lower alkyl or halo lower alkyl, it usually contains from 1 to 4 carbon atoms. When R is cycloalkyl or halo cycloalkyl it usually contains from 3 to 6 carbon atoms. R is preferably secondary-butyl, tertiary-butyl, cyclopropyl, or cyclohexyl.

An important class falling within the generic invention is represented by the formula:

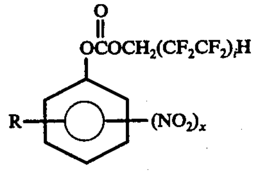
(III)

wherein:

- $x$ is 1, 2, or 3;
- $i$ is an integer ranging from 1 to 7, more often ranging from 1 to 5; and
- R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. Preferably when R is lower cycloalkyl or halo lower cycloalkyl, it usually contains from 3 to 6 carbon atoms. R is preferably secondary-butyl, tertiary-butyl, cyclohexyl, or cyclopropyl.

The nitro groups and R may be located in any position on the ring. Often the ring is substituted by two nitro groups which are usually in the 2',4'-positions while R is usually located in the 6'-position. This results in the subclass:

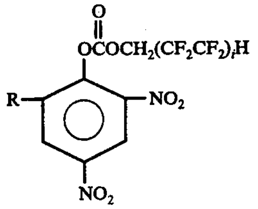
(IV)

wherein:

- $i$ is an integer ranging from 1 to 7, more often ranging from 1 to 5; and
- R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 3 to 6 carbon atoms. R is preferably secondary-butyl, tertiary-butyl, cyclohexyl or cyclopropyl.

Of especial importance are the compounds 2',4'-dinitro-6'-sec-butylphenyl 2,2,3,3-tetrafluoropropyl carbonate:

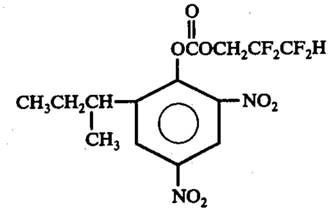
(V)

and 2',4'-dinitro-6'-cyclohexylphenyl 2,2,3,3-tetrafluoropropyl carbonate:

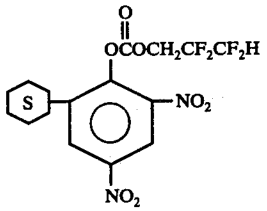
(VI)

Another important class falling within the generic invention is represented by the formula:

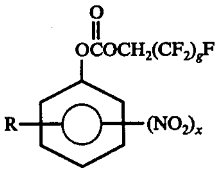
(VII)

wherein:

- $x$ is 1, 2, or 3;
- $g$ is an integer ordinarily ranging from 1 to 14 and, most often, from 1 to 11 or 4 to 11; and R is lower alkyl or halo lower alkyl ordinarily containing from 1 to 8 carbon atoms or lower cycloalkyl or halo lower cycloalkyl containing from 3 to 8 carbon atoms. When R is lower alkyl or halo lower alkyl, it usually contains from 1 to 4 carbon atoms. When R is lower cycloalkyl or halo lower cycloalkyl, it usually contains from 3 to 6 carbon atoms. R is preferably secondary-butyl, tertiary-butyl, cyclohexyl, or cyclopropyl.

The nitro groups and R may be located in any position on the ring. Often the ring is substituted by two nitro groups which are usually in the 2',4'-positions while R is usually located in the 6'-position. This results in the subclass:

(VIII)

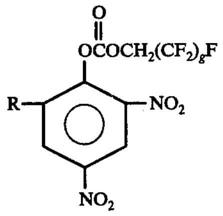

wherein:

*g* is an integer ordinarily ranging from 1 to 14, and most often, from 1 to 11 or 4 to 11; and R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 3 to 6 carbon atoms. R is preferably secondary-butyl, tertiary-butyl, cyclopropyl or cyclohexyl.

Of importance is the compound 2', 4'-dinitro-6'-sec-butylphenyl 2,2,2-trifluoroethyl carbonate:

(IX)

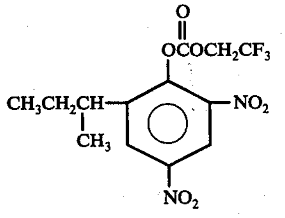

Still another important class falling within the generic invention is represented by the formula:

(X)

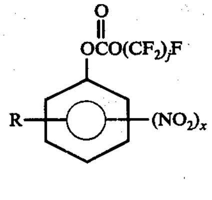

wherein:

*x* is 1, 2, or 3;

*j* is an integer ranging from 1 to 15, more often ranging from 2 to 11 or 3 to 11; and R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 3 to 6 carbon atoms. R is preferably secondary-butyl, tertiary-butyl, cyclohexyl, or cyclopropyl.

The nitro groups and R may be located in any position on the ring. Often the ring is substituted by two nitro groups which are usually in the 2',4'-positions while R is usually located in the 6'-position. This results in the subclass:

(XI)

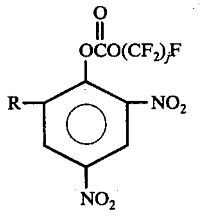

wherein:

*j* is an integer ordinarily ranging from 1 to 15, more often, from 2 to 11 or 3 to 11; and R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 3 to 6 carbon atoms. R is preferably secondary-butyl, tertiary-butyl, cyclohexyl, or cyclopropyl.

Compounds which exemplify the carbonates of the invention are:

(a) Those in which *x* is 1 and R is one of the groups mentioned herein:

2'-nitro-4'-methylphenyl fluoromethyl carbonate;
2'-nitro-4'-pentylphenyl 2,2,2-trifluoroethyl carbonate;
2'-nitro-5'-(1-chloromethylethyl)phenyl 2-(2,2,2-trifluoroethyl)-4,4,4-trifluorobutyl carbonate;
2'-nitro-5'-(2,4-dimethylhexyl)phenyl 1H,1H,9H-hexadecafluorononyl carbonate;
2'-nitro-5'-cyclooctylphenyl 1H,1H,13H-tetracosafluorotridecyl carbonate;
2'-nitro-6'-sec-butylphenyl perfluoroethyl carbonate;
2'-nitro-6'-trifluoromethylphenyl 8,8,8-trifluorooctyl carbonate;
2'-nitro-6'-sec-butylphenyl 1H,1H,15H-octacosafluoropentadecyl carbonate;
2'-nitro-6'-ethylphenyl 1,2-difluoroethyl carbonate;
2'-nitrophenyl perfluoropropyl carbonate;
3'-nitro-2'-ethylphenyl 2,2,2-trifluoroethyl carbonate;
3'-nitro-2'-sec-butylphenyl 3,3-difluoro-2-propenyl carbonate;
3'-nitro-2'-propylphenyl 1,1,3,3,6,6-hexafluorooctyl carbonate;
3'-nitro-5'-vinylphenyl 3,3,4,4-tetrafluorobutyl carbonate;
3'-nitro-5'-methylphenyl 1H,1H-tridecafluoroheptyl carbonate;
3'-nitro-5'-isopropylphenyl 1H,1H,5H-octafluoropentyl carbonate;
4'-nitro-2'-methylphenyl trifluoromethyl carbonate;
4'-nitro-2'-ethylphenyl 3,3-bis(pentafluoroethyl)-1,1,2,2,4,4,5,5,6,6,6-undecafluorohexyl carbonate;
4'-nitro-3'-propylphenyl 2-fluoroethyl carbonate;

4'-nitro-3'-ethylphenyl 12-fluorotetradecyl carbonate;

4'-nitro-3'-methylphenyl perfluorovinyl carbonate;

4'-nitro-3'-(2,4,6-trifluorocyclohexyl)phenyl 1H,1H,5H-octafluoropentyl carbonate;

4'-nitro-3'-(3-methylheptyl)phenyl 2,2-difluorobutyl carbonate; and

4'-nitro-6-cyclopropylphenyl 2-fluoroethyl carbonate.

(b) Those in which $x$ is 2 and R is one of the groups mentioned herein:

2',3'-dinitro-4'-methylphenyl perfluoropropyl carbonate;

2',3'-dinitro-4'-(methylthio)phenyl 3,3-bis(trifluoromethyl)-4,4,4-trifluorobutyl carbonate;

2',3'-dinitro-5'-sec-butylphenyl perfluoropentadecyl carbonate;

2',3'-dinitro-5'-(methylthio)phenyl 3-fluorobutyl carbonate;

2',3'-dinitro-5'-isopropylphenyl 1H,1H,7H-dodecafluoroheptyl carbonate;

2',3'-dinitro-5'-heptylphenyl 2,3-difluoropentyl carbonate;

2',3'-dinitro-5'-methylphenyl fluoromethyl carbonate;

2',3'-dinitro-6'-sec-butylphenyl 1,2,2-trifluoroethyl carbonate;

2',4'-dinitrophenyl 2,2,3,3-tetrafluoropropyl carbonate;

2',4'-dinitro-6'-sec-butylphenyl 2,2,3,3-tetrafluoropropyl carbonate;

2',4'-dinitro-6'-methylphenyl perfluoro-4-octynyl carbonate;

2',4'-dinitro-3'-methylphenyl 3-fluoropropyl carbonate;

2',4'-dinitro-3'-(2-chloroethyl)phenyl 4,7-difluoroheptyl carbonate;

2',4'-dinitro-3'-butylphenyl 1,1,4,4,8,10-hexafluoro-6-(1,2,2-trifluoroethyl)undecyl carbonate;

2',4'-dinitro-3'-pentafluorocyclohexylphenyl 2,2,3,3-tetrafluoropropyl carbonate;

2',4'-dinitro-5'-allylphenyl 1,3-difluoropropyl carbonate;

2',4'-dinitro-5'-(2-fluoroethyl)phenyl 1-fluoropropyl carbonate;

2',4'-dinitro-5'-isopropylphenyl 2,2,2-trifluoroethyl carbonate;

2',4'-dinitro-5'-ethylphenyl 1-(fluoromethyl)-2-fluoroethyl carbonate;

2',4'-dinitro-6'-methylphenyl 2,2,2-trifluoroethyl carbonate;

2',4'-dinitro-6'-methylphenyl 2,2,3,3-tetrafluoropropyl carbonate;

2',4'-dinitrophenyl 1H,1H,9H-hexadecafluorononyl carbonate;

2',4'-dinitro-6'-pentylphenyl 1H,1H,9H-hexadecafluorononyl carbonate;

2',4'-dinitro-6'-ethylphenyl 2,2,2-trifluoroethyl carbonate;

2',4'-dinitro-6'-ethylphenyl 4-fluoro-2-butynyl carbonate;

2',4'-dinitro-6'-isopropylphenyl 2,2,3,3-tetrafluoropropyl carbonate;

2',4'-dinitro-6'-ethylphenyl perfluorodecyl carbonate;

2',4'-dinitro-6'-isobutylphenyl 2,2-difluorobutyl carbonate;

2',4'-dinitro-6'-isobutylphenyl 2,2,3,3-tetrafluoropropyl carbonate;

2',4'-dinitro-6'-sec-butylphenyl 1-(trifluoromethyl)-2,2,2-trifluoroethyl carbonate;

2',4'-dinitro-6'-sec-butylphenyl 2,2,4,4,6,6,8,8,9,9-decafluoro 8-nonenyl carbonate;

2',4'-dinitro-6'-sec-butylphenyl fluoromethyl carbonate;

2',4'-dinitro-6'-sec-butylphenyl difluoromethyl carbonate;

2',4'-dinitro-6'-sec-butylphenyl trifluoromethyl carbonate;

2',4'-dinitro-6'-sec-butylphenyl 2-fluoroethyl carbonate;

2',4'-dinitro-6'-sec-butylphenyl 2,2-difluoroethyl carbonate;

2',4'-dinitro-6'-sec-butylphenyl 2,2,2-trifluoroethyl carbonate;

2',4'-dinitro-6'-sec-butylphenyl 2,2,3,3-tetrafluoropropyl carbonate;

2',4'-dinitro-6'-sec-butylphenyl 1H,1H,5H-octafluoropentyl carbonate;

2',4'-dinitro-6'-sec-butylphenyl 1H,1H,7H-dodecafluoroheptyl carbonate;

2',4'-dinitro-6'-sec-butylphenyl 1H,1H,9H-hexadecafluorononyl carbonate;

2',4'-dinitro-6'-sec-butylphenyl 1H,1H,11H-eicosafluoroundecyl carbonate;

2',4'-dinitro-6'-sec-butylphenyl 1H,1H,13H-tetracosafluorotridecyl carbonate;

2',4'-dinitro-6'-sec-butylphenyl 1H,1H,15H-octacosafluoropentadecyl carbonate;

2',4'-dinitro-6'-sec-butylphenyl perfluoropentadecyl carbonate;

2',4'-dinitro-6'-sec-butylphenyl 1H,1H,4H-docosafluorododecyl carbonate;

2',4'-dinitro-6'-sec-butylphenyl 2,2,3,3,3-pentafluoropropyl carbonate;

2',4'-dinitro-6'-sec-butylphenyl 1H,1H-nonafluoropentyl carbonate;

2',4'-dinitro-6'-sec-butylphenyl 1H,1H-undecafluorohexyl carbonate;

2',4'-dinitro-6'-sec-butylphenyl 1H,1H-tridecafluoroheptyl carbonate;

2',4'-dinitro-6'-sec-butylphenyl 1H,1H-pentadecafluorooctyl carbonate;

2',4'-dinitro-6'-sec-butylphenyl 1H,1H-heptadecafluorononyl carbonate;

2',4'-dinitro-6'-sec-butylphenyl 1H,1H-nonadecafluorodecyl carbonate;

2',4'-dinitro-6'-sec-butylphenyl 1H,1H-heneicosafluoroundecyl carbonate;

2',4'-dinitro-6'-sec-butylphenyl 1H,1H-tricosafluorododecyl carbonate;

2',4'-dinitro-6'-sec-butylphenyl 1H,1H-pentacosafluorotridecyl carbonate;

2',4'-dinitro-6'-sec-butylphenyl 1H,1H-heptacosafluorotetradecyl carbonate;

2',4'-dinitro-6'-sec-butylphenyl 1H,1H-nonacosafluoropentadecyl carbonate;

2',4'-dinitro-6'-sec-butylphenyl trifluoromethyl carbonate;

2',4'-dinitro-6'-sec-butylphenyl perfluoroethyl carbonate;

2',4'-dinitro-6'-sec-butylphenyl perfluoropropyl carbonate;

2',4'-dinitro-6'-sec-butylphenyl perfluorobutyl carbonate;

2',4'-dinitro-6'-sec-butylphenyl perfluoropentyl carbonate;

2',4'-dinitro-6'-sec-butylphenyl perfluorohexyl carbonate;
2',4'-dinitro-6'-sec-butylphenyl perfluoroheptyl carbonate;
2',4'-dinitro-6'-sec-butylphenyl perfluorooctyl carbonate;
2',4'-dinitro-6'-sec-butylphenyl perfluorononyl carbonate;
2',4'-dinitro-6'-sec-butylphenyl perfluorodecyl carbonate;
2',4'-dinitro-6'-sec-butylphenyl perfluoroundecyl carbonate;
2',4'-dinitro-6'-sec-butylphenyl perfluorododecyl carbonate; 2',4'-dinitro-6'-sec-butylphenyl perfluorotridecyl carbonate;
2',4'-dinitro-6'-sec-butylphenyl perfluorotetradecyl carbonate;
2',4'-dinitro-6'-sec-butylphenyl perfluoropentadecyl carbonate;
2',4'-dinitro-6'-sec-butylphenyl 3,3-bis(trifluoromethyl)-1,1,2,2,4,4,5,5,5-nonafluoropentyl carbonate;
2',4'-dinitro-6'-sec-butylphenyl 1,1,2,2,3,3,4,4-octakis(trifluoromethyl)-5,5,5-trifluoropentyl carbonate;
2',4'-dinitro-6'-sec-butylphenyl 3-(pentafluoroethyl)-2,2,4,4-tetrakis(trifluoromethyl)-2,2,5,5,5-pentafluoropentyl carbonate;
2',4'-dinitro-6'-sec-butylphenyl 3,5,7-tris(trifluoromethyl)-1,1,2,2,3,4,4,5,6,6,7,8,8,8-tetradecafluorooctyl carbonate;
2',4'-dinitro-6'-sec-butylphenyl 1-trifluoromethyl-2,2,2-trifluoroethyl carbonate;
2',4'-dinitro-6'-tert-butylphenyl 2,2,3,3-tetrafluoropropyl carbonate;
2',4'-dinitro-6'-cyclopropylphenyl 2,2,2-trifluoroethyl carbonate;
2',4'-dinitro-6'-cyclobutylphenyl 2,2,2-trifluoroethyl carbonate;
2',4'-dinitro-6'-cyclopentylphenyl 2,2,2-trifluoroethyl carbonate;
2',4'-dinitro-6'-cyclohexylphenyl 2,2,2-trifluoroethyl carbonate;
2',4'-dinitro-6'-cycloheptylphenyl 2,2,2-trifluoroethyl carbonate;
2',4'-dinitro-6'-cyclooctylphenyl 2,2,2-trifluoroethyl carbonate;
2',4'-dinitro-6'-cyclopropylphenyl 2,2,3,3-tetrafluoropropyl carbonate;
2',4'-dinitro-6'-cyclobutylphenyl 2,2,3,3-tetrafluoropropyl carbonate;
2',4'-dinitro-6'-cyclopentylphenyl 2,2,3,3-tetrafluoropropyl carbonate;
2',4'-dinitro-6'-cyclohexylphenyl 1-(trifluoromethyl)-2,2,2-trifluoroethyl carbonate;
2',4'-dinitro-6'-cyclohexylphenyl 2,2,3,3-tetrafluoropropyl carbonate;
2',4'-dinitro-6'-cyclohexylphenyl 1H,1H,5H-octafluoropentyl carbonate;
2',4'-dinitro-6'-cyclohexylphenyl 1H,1H,7H-dodecafluoroheptyl carbonate;
2',4'-dinitro-6'-cyclohexylphenyl 1H,1H,9H-hexadecafluorononyl carbonate;
2',4'-dinitro-6'-cyclohexylphenyl 1H,1H,11H-eicosafluoroundecyl carbonate;
2',4'-dinitro-6'-cyclohexylphenyl 1H,1H,13H-tetracosafluorotridecyl carbonate;
2',4'-dinitro-6'-cyclohexylphenyl 1H,1H,15H-octacosafluoropentadecyl carbonate;
2',4'-dinitro-6'-cycloheptylphenyl 2,2,3,3-tetrafluoropropyl carbonate;
2',4'-dinitro-6'-cyclooctylphenyl 2,2,3,3-tetrafluoropropyl carbonate;
2',4'-dinitro-6'-(4-fluorocycloheptyl)phenyl 2,2,3,3-tetrafluoropropyl carbonate;
2',4'-dinitro-6'-ethylphenyl 1H,1H,13H-tetracosafluorotridecyl carbonate;
2',4'-dinitro-6'-(methylthio)phenyl 1H,1H,13H-docosafluoro-9-tridecenyl carbonate;
2',4'-dinitro-6'-allylphenyl 2,2,4,4-tetrafluorohexyl carbonate;
2',4'-dinitro-6'-octylphenyl 1H-pentafluoropropyl carbonate;
2',4'-dinitro-6'-sec-butylphenyl 1H-pentafluoropropyl carbonate;
2',4'-dinitro-6'-sec-butylphenyl perfluoropropyl carbonate;
2',4'-dinitro-6'-pentylphenyl 1,1-bis(trifluoroethyl)-2,2,2-trifluoroethyl carbonate;
2',4'-dinitro-6'-propylphenyl 2,2-bis(trifluoromethyl)-3,3,3-trifluoropropyl carbonate;
2',4'-dinitro-6'-methylphenyl 4-fluoropentyl carbonate;
2',4'-dinitro-6'-sec-butylphenyl 2-(2-fluoroethyl)-3-[1-(difluoromethyl)-3,3-(difluoro)butyl]-4,7,7-trifluoro-5-methylheptyl carbonate;
2',4'-dinitro-6'-(vinylthio)phenyl perfluorobutyl carbonate;
2',4'-dinitro-6'-(4-butenyl)phenyl 2,2-difluoroethyl carbonate;
2',4'-dinitro-(4,4-difluoro-4-butenyl)phenyl 3,3,3-trifluoropropyl carbonate;
2',4'-dinitro-6'-ethylphenyl 1-trifluoromethyl-2,2-difluoroethyl-3-(1,1,2,2-tetrafluoroethyl)-1,3,4,4,5,5,5-heptafluoropentyl carbonate;
2',4'-dinitro-6'-neopentylphenyl 1H,1H,9H-hexadecafluorononylcarbonate;
2',4'-dinitro-6'-butylphenyl fluoromethyl carbonate;
2',5'-dinitro-3'-methylphenyl trifluoromethyl carbonate;
2',5'-dinitro-3'-sec-butylphenyl 1H,1H,7H-dodecafluoroheptyl carbonate;
2',5'-dinitro-4'-heptylphenyl 1H,1H,7H-dodecafluoroheptyl carbonate;
2',5'-dinitro-4'-(4-chlorocyclohexyl)phenyl 1H,1H,7H-dodecafluoroheptyl carbonate;
2',5'-dinitro-4'-(fluoromethylthio)phenyl 2,2-difluoroethyl carbonate;
2',5'-dinitro-6'-(trifluoromethyl)phenyl trifluoromethyl carbonate;
2',5'-dinitro-6'-ethylphenyl trifluoromethyl carbonate;
2',5'-dinitro-6'-[1-(trifluoromethyl)-2,2,2-(trifluoro)-ethylthio]phenyl perfluoro-10-tetradecenyl carbonate;
2',5'-dinitro-6'-isopropylphenyl perfluoroethyl carbonate;
2',6'-dinitrophenyl 2,2,3,3-tetrafluoropropyl carbonate;
2',6'-dinitro-3'-isohexylphenyl 1H,1H,9H-hexadecafluorononyl carbonate;
2',6'-dinitro-3'-ethylphenyl 1H,1H-heneicosafluoroundecyl carbonate;
2',6'-dinitro-3'-propylphenyl 2-fluoropropyl carbonate;
2',6'-dinitro-4'-(methylthio)phenyl 2,2,3,3-tetrafluoropropyl carbonate;

2',6'-dinitro-4'-ethylphenyl perfluorohexyl carbonate;

2',6'-dinitro-4'-tert-butylphenyl 3,5,7,10,12,14-hexafluoro-8-pentadecynyl carbonate;

2',6'-dinitro-4'-isopropylphenyl 1,2-difluoroethyl carbonate;

2',6'-dinitro-4'-isobutylphenyl perfluoropropyl carbonate;

3',4'-dinitro-2'-methylphenyl 1H,1H,7H-dodecylfluoroheptyl carbonate;

3',4'-dinitro-2'-(chloromethyl)phenyl 1,1,3,3,5,5-hexafluoropentyl carbonate;

3',4'-dinitro-5'-methylphenyl 2,2,3,3-tetrafluoropropyl carbonate;

3',4'-dinitro-5'-ethylphenyl 1,1,2,2,4,4,5,5,5-nonofluoro-3,3-bis(pentafluoroethyl)pentyl carbonate;

3',4'-dinitro-5'-butylphenyl perfluorohexyl carbonate;

3',4'-dinitro-5'-sec-butylphenyl 1H,1H,5H-octafluoropentyl carbonate;

3',4'-dinitro-6'-isopropylphenyl 1H,1H,13H-tetracosafluorotridecyl carbonate;

3',4'-dinitro-6'-(2,4,6,8-tetrafluorocyclooctyl)phenyl 2,2,3,3-tetrafluoropropyl carbonate;

3',4'-dinitro-6'-methylphenyl 1H,1H,13H-tetracosafluorotridecyl carbonate;

3',4'-dinitro-6'-isopropylphenyl 1,1,2-tris(trifluoromethyl)-2,3,3,3-tetrafluoropropyl carbonate;

3',4'-dinitro-6'-sec-butylphenyl difluoromethyl carbonate;

3',5'-dinitrophenyl 1,2-difluoroethyl carbonate;

3',5'-dinitro-2'-(fluoromethyl)phenyl 1H,1H,5H-octafluoropentyl carbonate;

3',5'-dinitro-2'-(bromomethyl)phenyl 1H,1H,5H-octafluoropentyl carbonate;

3',5'-dinitro-4'-methylphenyl perfluoroheptyl carbonate;

3',5'-dinitro-4'-(methylthio)phenyl trifluoromethyl carbonate; and

3',5'-dinitro-4'-isopropylphenyl difluoromethyl carbonate.

(c) Those in which $x$ is 3 and R is one of the groups mentioned herein:

2',3',4'-trinitro-5'-methylphenyl 1H,1H,5H-octafluoropentyl carbonate;

2',3',4'-trinitro-5'-ethylphenyl 1,2-difluoroethyl carbonate;

2',3',4'-trinitro-6'-ethylphenyl 3-fluoropentyl carbonate;

2',3',4'-trinitro-6'-methylphenyl 1H,1H,15H-octacosafluoropentadecyl carbonate;

2',3',4'-trinitro-6'-methylphenyl 2,2,2-trifluoroethyl carbonate;

2',3',5'-trinitro-4'-methylphenyl 1H,1H,6H,12H-heneicosafluorododecyl carbonate;

2',3',5'-trinitro-4'-pentachlorocyclopropylphenyl trifluoromethyl carbonate;

2',3',5'-trinitro-4'-propylphenyl 3,3,4-trifluorobutyl carbonate;

3',3',5'-trinitro-4'-trifluoromethylphenyl 1H,1H-undecafluorohexyl carbonate;

2',3',5'-trinitro-6'-methylphenyl fluoromethyl carbonate;

2',3',6'-trinitro-4-isopropylphenyl 1H,1H,11H-eicosafluoroundecyl carbonate;

2',3',6'-trinitro-4'-(4,4,4-trifluoro-2-butenylthio)phenyl trifluoromethyl carbonate;

2',3',6'-trinitro-4'-(ethylthio)phenyl 1,2,3-trifluoropropyl carbonate;

2',3',6'-trinitro-5'-isopropylphenyl 1H,2H,13H-tetracosafluorotridecyl carbonate;

2',3',6'-trinitro-5'-isopropylphenyl 1H,1H,13H-tetracosafluorotridecyl carbonate;

2',3',6'-trinitro-5'-methylphenyl 1,2-difluoroethyl carbonate;

2',4',5'-trinitro-3'-methylphenyl perfluoroethyl carbonate;

2',4',5'-trinitrophenyl 2,2,2-trifluoroethyl carbonate;

2',4',5'-trinitro-6'-sec-butylphenyl trifluoromethyl carbonate;

2',4',5'-trinitro-6'-isopropylphenyl 1,2,3,4,5,6-hexafluorohexyl carbonate;

2',4',5'-trinitro-6'-methylphenyl 2-fluoroethyl carbonate;

2',4',6'-trinitro-3'-ethylphenyl 2-fluoropropyl carbonate;

2',4',6'-trinitro-3'-methylphenyl 1H,1H,9H-hexadecafluorononyl carbonate;

2',4',6'-trinitro-3'-methylphenyl perfluoroheptyl carbonate;

3',4',5'-trinitro-2'-methylphenyl 2,2,3,3-tetrafluoropropyl carbonate;

3',4',5'-trinitro-2'-sec-butylphenyl 1,2-difluoroethyl carbonate; and

3',4',5'-trinitro-2'-isopropylphenyl 1H,1H,11H-eicosafluoroundecyl carbonate.

These carbonates are prepared as described in the Grandparent application, application Ser. No. 76,275, filed Sept. 28, 1970, and now U.S. Pat. No. 3,742,010, which application is incorporated herein by reference and made a part hereof, as well as in applications: Ser. No. 299,968, filed Oct. 24, 1972, now U.S. Pat. No. 3,852,464, issued Dec. 3, 1974; Ser. No. 505,419, filed Sept. 12, 1974, and now U.S. Pat. No. 4,022,609, issued May 10, 1977; which applications are incorporated herein by reference and made a part hereof.

The fluorinated alkenyl chloroformates and flourinated alkynyl chloroformates may be prepared by methods analogous to those for preparing the fluorinated alkyl chloroformates.

In general, the carbonates of this invention possess properties which make them useful as fungicides. Fungi may be killed by bringing a fungicidal amount of the carbonate and the fungi into mutual contact, as for example, by applying certain carbonates directly to the fungi. In another embodiment the carbonate of general formulas is applied to a region where fungi are likely to be found in order to preclude fungi from becoming established. The concentration of the carbonate compound in the formulation used to control pathogenic fungi or prevent their establishment and the total amount applied will vary depending upon the particular carbonate being employed and the particular fungus being confronted.

The type of formulation used may vary. Solutions and suspensions of the carbonate are effective. The usual method of applying solutions or suspensions is to drench the area of application. Sprays, showers, mists, and dips may be used for this purpose. When some of the more active carbonates are used, particularly at higher concentrations, a complete drenching is not necessary. Mists are often used where a drench is not desired.

The carbonate formulations of the invention may also be applied in the form of a powder or dust. These powders or dusts may contain diluents such as, for example, aluminum silicate, bentonite, calcium carbonate, calcium silicate, diatomaceous silica, hydrated lime, pulverized limestone, montmorillinite, pulverized phosphate rock, silica, talc, or vermiculite.

The concentration of the carbonate compound in the formulation and the total amount applied will vary depending upon the particular carbonate being employed and the particular pathogenic fungus being confronted. Other factors such as season of the year, environmental conditions, and stage of fungi development all have their effect. Exemplary concentrations employed range from about 1 to about 5000 parts per million by weight (ppm) for protectant applications. Usually the concentration will range from about 10 to about 1000 ppm for protectant and eridicant applications. Concentrations of from about 10 to about 250 ppm are most often used for protectant and eridicant applications. Liquid formulations having such concentrations are ordinarily applied until the area of application is well wetted. Dusts of formulations having these concentrations are typically applied until a light coating of powder appears on the area being treated.

The following specific embodiments illustrate, by way of example, the basic principles of the present invention.

EXAMPLE I

When possible, the test compounds are formulated as follows:

A stock acetone emulsion is prepared having the following composition by weight: 99.75 percent acetone, 0.20 percent sorbitan trioleate (SPAN 85 ®), and 0.05 percent sorbitan monooleate polyoxyalkylene derivative (TWEEN 80 ®). Test compound is dissolved in a portion of the stock acetone emulsion. Deionized water is added to yield a concentrated test solution containing about 10 percent acetone, 0.020 percent SPAN 85 ®, and 0.0050 percent TWEEN 80 ®. The amount of test compound dissolved in the stock acetone emulsion is such that when diluted with deionized water the concentrated test solution has the highest concentration (usually 1,000 ppm) of test compound used in the tests. Other solutions are prepared by diluting the concentrated test solution with a mixture of deionized water and stock acetone emulsion, which mixture contains about 10 percent acetone, 0.020 percent SPAN 85 ®, and 0.0050 percent TWEEN 80 ®. Thus, all test solutions always contain about 10 percent acetone, 0.020 percent SPAN 85 ®, and 0.0050 percent TWEEN 80 ®, irrespective of the concentration of test compound. Compounds giving an unsatisfactory formulation as an acetone emulsion are formulated as wettable powders and diluted with water and wetting agent before application.

Test compounds are formulated for fungicidal testing as described above, and Cheyenne wheat plants (*Triticum vulgare*), approximately 7 to 8 days old and 4 to 5 inches tall are mounted on a compound turntable and sprayed with the test formulations at the concentrations indicated. The wheat plants are thoroughly wetted with the test formulation. After drying, the treated wheat plants are dusted with spores of Leaf Rust of Wheat (*Puccinia rubigo-vera*) directly from diseased plants and then immediately placed in an incubation chamber maintained at 70° F. and a relative humidity greater than 95 percent. After an overnight incubation period, the test plants are removed to the greenhouse where they are held for a period of 3 to 5 days for disease development. Control plants are similarly processed except that they are not treated with test compound. After the disease development period, the pustules developed on both the inoculated but otherwise untreated control plants and the inoculated and treated plants are counted. Data is reported as Percent Control which is computed in accordance with the following formula:

$$\text{Percent Control} = \left(1.0 - \frac{\text{avg. no. pustules on treated plants}}{\text{avg. no. pustules on untreated plants}}\right) \times 100$$

Table 1 reports observed results where the test compound is 2′,4′-dinitro-6′-cyclohexylphenyl 2,2,3,3-tetrafluoropropyl carbonate.

TABLE 1

Fungicidal Effectiveness of 2′,4′-Dinitro-6′-cyclohexyphenyl 2,2,3,3-Tetrafluoropropyl Carbonate as Protectant Against Leaf Rust of Wheat (*Puccinia rubigo-vera*)

| Concentration ppm | Percent Control |
|---|---|
| 1,000 | 100 |
| 250 | 100 |
| 100 | 100 |
| 50 | 99, 100 |
| 25 | 81 |
| 10 | 30 |

EXAMPLE II

The procedure of Example I is followed except that the test compound is 2′,4′-dinitro-6′-sec-butylphenyl 2,2,3,3-tetrafluoropropyl carbonate. Table 2 reports the observed results of this case.

TABLE 2

Fungicidal Effectiveness of 2′,4′-Dinitro-6′-sec-butylphenyl 2,2,3,3-Tetrafluoropropyl Carbonate as Protectant Against Leaf Rust of Wheat (*Puccinia rubigo-vera*)

| Concentration ppm | Percent Control |
|---|---|
| 1,000 | 100 |
| 100 | 95 |
| 50 | 100 |
| 25 | 92 |
| 10 | 69 |

EXAMPLE III

The procedure of Example I is followed except that the test compound is 2′,4′-dinitro-6′-methylphenyl 2,2,3,3-tetrafluoropropyl carbonate. Table 3 reports the observed results of the test.

TABLE 3

Fungicidal Effectiveness of 2′,4′-Dinitro-6′-methylphenyl 2,2,3,3-Tetrafluoropropyl Carbonate as Protectant Against Leaf Rust of Wheat (*Puccinia rubigo-vera*)

| Concentration ppm | Percent Control |
|---|---|
| 1,000 | 100 |
| 250 | 100 |
| 100 | 100 |
| 50 | 45 |

EXAMPLE IV

The procedure of Example I is followed except that the test compound is 2′,4′-dinitro-6′-sec-butylphenyl 2,2,2-trifluoroethyl carbonate. Table 4 reports the observed results of the test.

TABLE 4

| Fungicidal Effectiveness of 2',4'-Dinitro-6'-sec-butylphenyl 2,2,2-Trifluoroethyl Carbonate as Protectant Against Leaf Rust of Wheat (*Puccinia rubigo-vera*) | |
|---|---|
| Concentration ppm | Percent Control |
| 1,000 | 100 |
| 250 | 99 |
| 100 | 69 |

EXAMPLE V

The procedure of Example I is followed except that the test compound is 2',4'-dinitro-6'-sec-butylphenyl 1H,1H,11H-eicosafluoroundecyl carbonate. Table 5 reports the observed results.

TABLE 5

| Fungicidal Effectiveness of 2',4'-Dinitro-6'-sec-butylphenyl 1H,1H,11H-Eicosafluoroundecyl Carbonate as Protectant Against Leaf Rust of Wheat (*Puccinia rubigo-vera*) | |
|---|---|
| Concentration ppm | Percent Control |
| 1,000 | 64 |

EXAMPLE VI

The procedure of Example I is followed except that the test compound is 2',4'-dinitro-6'-sec-butylphenyl 1-(trifluoromethyl)-2,2,2-trifluoroethyl carbonate. Table 6 reports the observed results.

TABLE 6

| Fungicidal Effectiveness of 2',4'-Dinitro-6'-sec-butylphenyl 1-(trifluoromethyl)-2,2,2-trifluoroethyl Carbonate as Protectant Against Leaf Rust of Wheat (*Puccinia rubigo-vera)* | |
|---|---|
| Concentration ppm | Percent Control |
| 1,000 | 100 |

EXAMPLE VII

The procedure of Example I is followed except that the test compound is 2',4'-dinitrophenyl 2,2,3,3-tetrafluoropropyl carbonate. Table 7 reports the observed results.

TABLE 7

| Fungicidal Effectiveness of 2',4'-Dinitrophenyl 2,2,3,3-Tetrafluoropropyl Carbonate as Protectant Against Leaf Rust of Wheat (*Puccinia rubigo-vera)* | |
|---|---|
| Concentration ppm | Percent Control |
| 1,000 | 100 |

EXAMPLE VIII

The procedure of Example I is followed except that the test compound is 2',6'-dinitrophenyl 2,2,3,3-tetrafluoropropyl carbonate. Table 8 reports the observed results.

TABLE 8

| Fungicidal Effectiveness of 2',6'-Dinitrophenyl 2,2,3,3-Tetrafluoropropyl Carbonate as Protectant Against Leaf Rust of Wheat (*Puccinia rubigo-vera* | |
|---|---|
| concentration ppm | Percent Control |
| 1,000 | 100 |

EXAMPLE IX

The procedure of Example I is followed except that the test compound is 2',4'-dinitro-6'-sec-butylphenyl 2-fluoroethyl carbonate. Table 9 reports the observed results.

TABLE 9

| Fungicidal Effectiveness of 2',4'-Dinitro-6'-sec-butylphenyl 2-Fluoroethyl Carbonate as Protectant Against Leaf Rust of Wheat (*Puccinia rubigo-vera*) | |
|---|---|
| Concentration ppm | Percent Control |
| 1,000 | 100 |

EXAMPLE X

The procedure of Example I is followed except that the test compound is 2',4'-dinitro-6'-tert-butylphenyl 2,2,3,3-tetrafluoropropyl carbonate. Table 10 reports the observed results.

TABLE 10

| Fungicidal Effectiveness of 2',4'-Dinitro-6'-tert-butylphenyl 2,2,3,3-Tetrafluoropropyl Carbonate as Protectant Against Leaf Rust of Wheat (*Puccinia rubigo-vera*) | |
|---|---|
| Concentration ppm | Percent Control |
| 1000 | 81 |

EXAMPLE XI

The procedure of Example I is followed except that the test compound is 2',4'-dinitro-6'-sec-butylphenyl 1H,1H,7H-dodecafluoroheptyl carbonate. Table 11 reports the observed results.

TABLE 11

| Fungicidal Effectiveness of 2',4'-Dinitro-6'-sec-butylphenyl 1H,1H,7H-dodecafluoroheptyl Carbonate as Protectant Against Leaf Rust of Wheat (*Puccinia, rubigo-vera*) | |
|---|---|
| Concentration ppm | Percent Control |
| 1,000 | 100 |

Many of the carbonates of this invention possess properties which make them useful for controlling pathogenic fungus. Pathogenic fungi are controlled by bringing a fungicidal amount of the carbonate and the fungi into mutual contact, as for example by applying the carbonate directly to the fungi. As used herein and in the claims, the phrase "pathogenic fungi are controlled" means that the pathogenic fungus, or fungi are either killed, or weakened, or their affects upon the plants (disease) is eliminated or greatly diminished. As used herein and in the claims, the phrase "bringing the fungi into mutual contact", refers to contacting the fungi directly with the carbonate by applying it to the fungi growing upon the plants that are desired to be protected (eridicant application). This method of applying a carbonate may be by dusting, spraying, or any of the other methods known to those skilled in the art for applying compositions to plants which are affected by the fungi.

In another embodiment, the carbonate is applied to a region where pathogenic fungi are likely to be found in order to preclude fungi from becoming established (protectant application). As used herein and in the claims, the phrase "applied to a region an effective amount, which prevents the establishment of said fungus, of a compound . . . ", refers to applying the carbonate to the plants which are to be protected from the pathogenic fungi, prior to the occurrence of the fungi upon the plants. Again this method of application is by any of the well known methods, such as spraying, and dusting.

The phrase "which prevents the establishment of said fungus", as used herein and in the claims means when the carbonate is applied to the plant before the fungi occurs, it acts as a protectant, that is it either remains upon the plant or possibly is absorbed by the plant so that the plant now becomes repellant to the pathogenic fungi in such a way that from 25 to 100 percent of the pathogenic fungus which lands upon the plants are killed by the chemical carbonate thereon, or when the fungus attempts to feed upon the plant the fungi is repelled or killed by the plant treated with the carbonate.

The phrase "a fungicidal amount of the carbonate" as used herein and in the claims refers to that amount of carbonate required in order to control the affect of the fungi upon the plant, either by eliminating the fungus from the plant (e.g., killing the fungi) or by completely or partially eliminating the affect of the fungus upon the plant, that is it partially or completely eliminates the disease caused by the fungus. This elimination of the effect of the fungus upon the plant is determined by comparing a plant which has been treated with the carbonate with plants which have not been treated with carbonate. Those plants that have been treated generally have from 20 to 100 percent decrease in the disease caused by the fungus. In other words the effect of the fungus upon the plant, or the fungus itself, it either eliminated completely (e.g., 100 percent control), or that a field having treated plants would show that the number of pustules of fungus would be 25 percent less than the number of pustules present in a field of untreated plants (25% control).

Compounds represented by the structural formulas are generally useful in preventing the establishment of pathogenic fungus population in a region (protectant application), particularly at the higher concentration rates mentioned herein. Those pathogenic fungus which are particularly affected by the compounds of general formula (I) are those of the genus *Puccinia, Piricularia, Erysiphe,* and *Phytophthora.* The compounds of general formula (I) are useful for the specific species of the above mentioned genera *Puccinia polysora, Puccinia sorghi, Puccinia rubigo-vera, Piricularia oryzoe, Erysiphe graminis, Erysiphe polygoni, Erysiphe cichora ceum,* and *Phytophthora infestans.*

Those compounds of general formula (I) wherein the value of $k$ is 2 are especially useful, particularly those in which the radical $-C_mH_{2m+k-1-n}$ is one of the preferred radicals of $-CH-(CF_3)_2$, $-CH_2CF_3$, $-CH_2CH_2F$, and $-CH_2CF_2CF_2H$. Those in which the value of $k$ is 2 and R is a lower alkyl of from 1 to 8 carbon atoms or a lower cycloalkyl of from 3 to 8 carbon atoms, are very useful, especially when the lower cycloalkyl is cyclohexyl or cyclopropyl and when the lower alkyl is sec-butyl or tert-butyl. Particularly useful are those in which the radical $-C_mH_{2m+k-1-n}$ is one of the preferred radicals mentioned herein.

Those compounds of general formula (I) which are of a particular use are those in which the value of $x$ is 2, with nitro groups located in the 2′,4′-positions and with R located in the 6′-position, particularly when the radical $-C_mH_{2m+k-1-n}$ is one of the preferred radicals mentioned herein, and R is one of the groups found very useful as set forth herein.

Those compounds of general formula (I) in which $k$ is 2 and $m$ is from 1 to 5, and $n$ is from 3 to 8 are of a special usefulness, and of these, those are especially preferred in which R is a lower alkyl of from 1 to 8 carbon atoms or a lower cycloalkyl of from 3 to 8 carbon atoms, particularly when the lower alkyl or the lower cycloalkyl is one of the preferred lower alkyl or lower cycloalkyl of cyclohexyl, cyclopropyl, sec-butyl, or tert-butyl; greatly preferred are those in which $x$ is 2, with the nitro groups located at the 2′,4′-positions and R is located in the 6′-position.

Of all of the compounds useful in the method of preventing the establishment of fungus, those compounds of 2′,4′-dinitro-6′-cyclohexylphenyl 2,2,3,3-tetrafluoropropyl carbonate, 2′,4′-dinitrophenyl 2,2,3,3-tetrafluoropropyl carbonate, 2′,6′-dinitrophenyl 2,2,3,3-tetrafluoropropyl carbonate, 2′,4′-dinitro-6′-sec-butylphenyl 2-fluoroethyl carbonate, 2′,4′-dinitro-6′-tert-butylphenyl 2,2,3,3-tetrafluoropropyl carbonate, and 2′,4′-dinitro-6′-sec-butylphenyl 1H,1H,7H-dodecafluoroheptyl carbonate are especially preferred for control of fungus, particularly fungus of the genus mentioned herein and especially for those specific fungus mentioned herein, and as shown in the specific examples, and particularly the fungus *Puccinia rubigo-vera, Erysiphe cichoraceum,* and *Puccinia carthami.*

Those compounds of 2′,4′-dinitro-6′-sec-butylphenyl 1-(trifluoromethyl)-2,2,2-trifluoroethyl carbonate; 2′,4′-dinitro-6′-sec-butylphenyl 2-fluoroethyl carbonate; 2′,4′-dinitrophenyl 2,2,3,3-tetrafluoropropyl carbonate; 2′,6′-dinitrophenyl 1-(trifluoromethyl)-2,2,2-trifluoroethyl carbonate; and 2′,4′-dinitro-6′-cyclohexylphenyl 2-fluoroethyl carbonate are used for the method of controlling pathogenic fungus of the genus Fusarium by bringing into mutual contact said fungus and a fungicidal amount of one of the compounds (eridicant application) especially the fungus *Fusarium oxysporum f. lycopersici.* Preferably the compound for eridicant application is 2′,4′-dinitro-6′-sec-butylphenyl 1-(trifluoromethyl)-2,2,2-trifluoroethyl carbonate. These compounds are generally used at rates from 1000 to 100 ppm, preferably from 500 to 100 ppm.

While the invention has been described with reference to certain illustrative embodiments, it is not intended that it shall be limited thereby except insofar as what appears in the accompanying claims.

We claim:

1. A method of controlling pathogenic fungus of the genus Fusarium which comprises bringing into mutual contact said fungus and a fungicidal amount of a compound selected from the group consisting of:

2′,4′-dinitro-6′-sec-butylphenyl 1-(trifluoromethyl)-2,2,2-trifluoroethyl carbonate, 2′,4′-dinitro-6′-sec-butylphenyl 2-fluoroethyl carbonate, 2′,4′-dinitrophenyl 2,2,3,3-tetrafluoropropyl carbonate, 2′,6′-dinitrophenyl 1-(trifluoromethyl)-2,2,2-trifluoroethyl carbonate, and 2',4'-dinitro-6'-cyclohexylphenyl 2-fluoroethyl carbonate.

2. The method of claim 1, wherein the pathogenic fungus is *Fusarium oxysporum f. lycopersici.*

3. The method of claim 2, wherein the compound is 2',4'-dinitro-6'-sec-butylphenyl 1-(trifluoromethyl)-2,2,2-trifluoroethyl carbonate.

4. The method of claim 1, wherein the compound is 2',4'-dinitro-6'-sec-butylphenyl 1-(trifluoromethyl)-2,2,2-trifluoroethyl carbonate.

5. A method of preventing the establishment of a pathogenic fungus population in a region free from mites which comprises applying to the region an effective amount, which prevents the establishment of said fungus, of a compound represented by the structural formula:

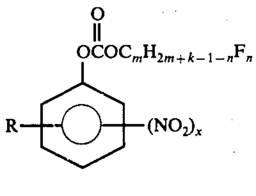

wherein:

$x$ is 1, 2, or 3;

$k$ is $-2$, 0, or 2;

$m$ is an integer ranging from 1 to 15 when $k$ is 2;

$m$ is an integer ranging from 2 to 15 when $k$ is 0 or $-2$;

$n$ is an integer ranging from 1 to $(2m+k-1)$; and

R is hydrogen, lower alkyl, halo lower alkyl, lower alkenyl, halo lower alkenyl, lower alkylthio, halo lower alkylthio, lower alkenylthio, halo lower alkenylthio, lower cycloalkyl, or halo lower cycloalkyl.

6. The method of claim 5, wherein the pathogenic fungus is selected from the genus group consisting of Puccinia, Piricularia, Erysiphe, and Phytophthora.

7. The method of claim 5, wherein the pathogenic fungus is a species selected from the group consisting of *Puccinia polysora, Puccinia sorghi, Puccinia rubigo-vera, Piricularia oryzoe, Erysiphe graminis, Erysiphe polygoni, Erysiphe cichoraceum,* and *Phytophthora infestans.*

8. The method of claim 7, wherein the value of $k$ is 2, $m$ is an integer ranging from 1 to 15, and $n$ is an integer ranging from 1 to 31.

9. The method of claim 8, wherein the radical $-C_mH_{2m+k-1-n}F_n$ is selected from the group of fluorinated radicals consisting of $-CH_2CF_3$, $-CH_2CH_2F$, $-CH_2CF_2CF_2H$, and $HC(CF)_3$.

10. The method of claim 9, wherein R is selected from the group consisting of a lower alkyl having from 1 to 8 carbon atoms, and a lower cycloalkyl having from 3 to 6 carbon atoms.

11. The method as recited in claim 10, wherein R is selected from the group consisting of cyclohexyl, cyclopropyl, sec-butyl, and tert-butyl.

12. The method of claim 11, wherein the value of $x$ is 2, the nitro groups are located in the 2',4'-positions, and R is located in the 6'-position.

13. The method as recited in claim 8, wherein the value of $x$ is 2, the nitro groups are located in the 2',4'-positions, and R is located in the 6'-position.

14. The method as recited in claim 13, wherein R is selected from the group consisting of a lower alkyl having from 1 to 4 carbon atoms, and a lower cycloalkyl having from 3 to 6 carbon atoms.

15. The method as recited in claim 14, wherein R is selected from the group consisting of cyclohexyl, cyclopropyl, sec-butyl, and tert-butyl.

16. The method of claim 13, wherein $m$ is from 1 to 5 and $n$ is from 3 to 8.

17. The method of claim 16, wherein $k$ is 2 and R is selected from the group consisting of a lower alkyl containing from 1 to 8 carbon atoms and a lower cycloalkyl containing from 3 to 6 carbon atoms.

18. The method as recited in claim 17, wherein R is selected from the group consisting of cyclohexyl, cyclopropyl, sec-butyl, and tert-butyl.

19. The method of claim 6, wherein $m$ is from 1 to 5 and $n$ is from 3 to 8.

20. The method of claim 19, wherein the value of $x$ is 2, the nitro groups are located in the 2',4'-positions, and R is located in the 6'-position.

21. The method of claim 7, wherein the compound is 2',4'-dinitrophenyl 2,2,3,3-tetrafluoropropyl carbonate.

22. The method of claim 7, wherein the compound is 2',6'-dinitrophenyl 2,2,3,3-tetrafluoropropyl carbonate.

23. The method as recited in claim 8, wherein the fungus is of the genus *Puccinia.*

24. The method as recited in claim 8, wherein the fungus is *Puccinia rubigo-vera.*

25. The method as recited in claim 6, wherein the compound is 2',4'-dinitro-6'-sec-butylphenyl 2-fluoroethyl carbonate.

26. The method as recited in claim 25, wherein the fungus is selected from the group consisting of *Puccinia rubigo-vera, Erysiphe cichoraceum,* and *Puccinia carthami.*

27. The method as recited in claim 7, wherein the compound is selected from the group consisting of 2',4'-dinitro-6'-tert-butylphenyl 2,2,3,3-tetrafluoropropyl carbonate, 2',4'-dinitro-6'-sec-butylphenyl 1H,1H,7H-dodecafluoroheptyl carbonate.

28. The method of claim 6, wherein the compound is 2',4'-dinitro-6'-sec-butylphenyl 1-(trifluoromethyl)-2,2,2-trifluoroethyl carbonate.

29. The method of claim 6, wherein the compound is 2',4'-dinitro-6'-sec-butylphenyl 1H,1H,7H-dodecafluoroheptyl carbonate.

30. The method of claim 6, wherein the value of $k$ is 2 and R is selected from the group consisting of lower alkyl containing from 1 to 8 carbon atoms and lower cycloalkyl containing from 3 to 8 carbon atoms.

31. The method of claim 30, wherein the value of $x$ is 2, the nitro groups are located in the 2',4'-positions, and R is located in the 6'-position.

32. The method of claim 6, wherein the compound is 2',4'-dinitro-6'-cyclohexylphenyl 2,2,3,3-tetrafluoropropyl carbonate.

33. The method of claim 6, wherein the compound is 2',4'-dinitro-6'-sec-butylphenyl 2,2,3,3-tetrafluoropropyl carbonate.

34. The method of claim 7, wherein the compound is 2',4'-dinitro-6'-sec-butylphenyl 1-(trifluoromethyl)-2,2,2-trifluoroethyl carbonate.

35. The method of claim 6, wherein the compound is 2',4'-dinitrophenyl 2,2,3,3-tetrafluoropropyl carbonate.

36. The method of claim 6, wherein the compound is 2',6'-dinitrophenyl 2,2,3,3-tetrafluoropropyl carbonate.

37. The method of claim 7, wherein the compound is 2',4'-dinitro-6'-sec-butylphenyl 2-fluoroethyl carbonate.

38. The method of claim 7, wherein the compound is 2',6'-dinitro-4'-sec-butylphenyl 2-fluoroethyl carbonate.

* * * * *